United States Patent [19]

Freers

[11] Patent Number: 4,950,487
[45] Date of Patent: Aug. 21, 1990

[54] TREATMENT, METHOD AND COMPOSITION FOR TREATING FUNGUS DISEASES OF DECIDUOUS TREES

[76] Inventor: Charles R. Freers, 2502 Lucas St., Muscatine, Iowa 52761

[21] Appl. No.: 310,853

[22] Filed: Feb. 13, 1989

Related U.S. Application Data

[63] Continuation of Ser. No. 580,829, Feb. 16, 1984, abandoned.

[51] Int. Cl.$^5$ ............................................. A01N 59/18
[52] U.S. Cl. ..................................... 424/645; 424/644
[58] Field of Search ................ 424/146, 145, 645, 644

[56] References Cited

U.S. PATENT DOCUMENTS

| | | | |
|---|---|---|---|
| 1,999,458 | 2/1934 | Hollister | 424/146 |
| 2,399,829 | 5/1946 | Salle et al. | 424/146 |
| 2,897,114 | 7/1959 | Sauls | 424/146 |
| 3,848,336 | 3/1976 | Stutz | 424/129 |
| 3,993,752 | 11/1976 | Stutz | 424/146 |

Primary Examiner—Douglas W. Robinson
Attorney, Agent, or Firm—Zarley, McKee, Thomte, Voorhees & Sease

[57] ABSTRACT

A method and composition for treating fungus diseases of deciduous trees which comprises introducing into the vascular system of the tree, a small but treating effective amount of an active composition of methanol in combination with a soluble inorganic mercury salt preferably mercuric chloride and a Pseudonomas bacterial nutrient.

13 Claims, 1 Drawing Sheet

TREATMENT, METHOD AND COMPOSITION FOR TREATING FUNGUS DISEASES OF DECIDUOUS TREES

CROSS REFERENCE TO A RELATED APPLICATION

This application is a continuation of application Ser. No. 580,829 filed Feb. 16, 1984, and now abandoned.

BACKGROUND OF THE INVENTION

One reoccurring problem which at times can be devastating to healthy deciduous trees is the infection of such trees by various fungi. When such an infection occurs, it can spread rapidly from tree to tree, and in short order wipe out an entire area of a given species. For example, certain of our midwestern cities have been wiped out by a common fungi disease referred to as Dutch Elm Disease, technically *Cerateocystis Ulmi*. Other equally common but perhaps less notorious diseases include oak wilt (Faegacaerum), sycamore decline, maple decline, including Norway maple, Crimson maple, red maple, and anthracnose in ash.

A common factor of the above mentioned diseases is that they can spread rapidly from tree to tree, and that they are all fungus diseases of deciduous trees. The ability of the disease to spread from tree to tree exaggerates the effect when, as is often the case, a given locality is populated densely with a single species.

The devastating effect of such fungus diseases on deciduous trees can be illustrated by the most famous of the diseases successfully treated by this invention, Dutch Elm Disease. In Dutch Elm Disease, the original infection with the fungus may come by transfer from a particular beetle species. Once one or more of the trees in a given population are infected, the fungus can then transfer through root chutes from tree to tree, causing infection of the entire population in a relatively short period of time. It is this phenomenon which has literally wiped out the Dutch Elm tree population in many midwestern cities.

Accordingly there is a real and continuing need for the development of an effective fungicide against *Cerateocystis Ulmi* and the other above mentioned fungus diseases.

There is also a real and continuing need for the development of an effective treatment which will act as a toxin to the fungus causing the above mentioned diseases of deciduous trees, while at the same time is not harmful to man and the surrounding environment.

This invention has as its primary objectives the fulfillment of the above needs.

Yet another objective of this invention is to develop and effective fungicide for fungus diseases of deciduous trees which utilizes as its active ingredient, methyl mercury organo complex ions, which are developed by metabolism in situ within the tree. This avoids exposure outside of the tree of the environment, and those doing the treating, to the highly lethal methyl mercury toxin.

The method and means of accomplishing each of the above objectives, as well as others, will become apparent from the detailed description of the invention which follows.

DETAILED DESCRIPTION OF THE PREFERRED EMBODIMENT

Figure 1:
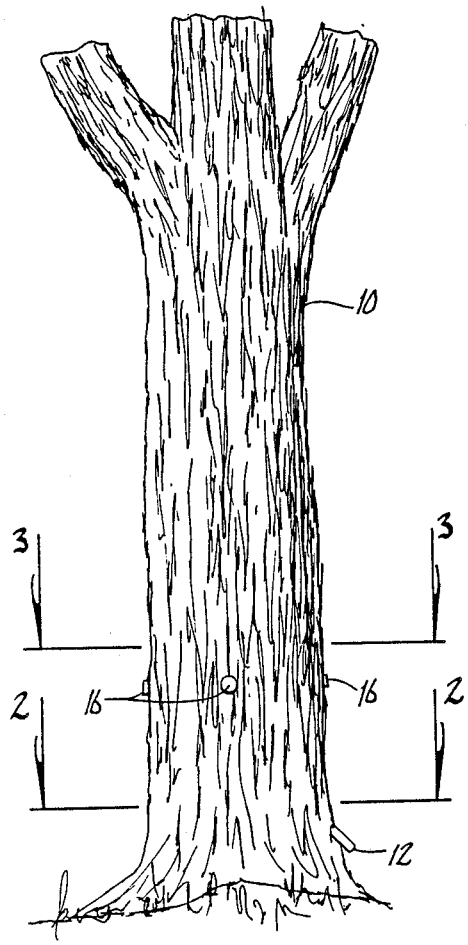
FIG. 1 shows a tree which has been treated for Dutch Elm.
Figure 2:
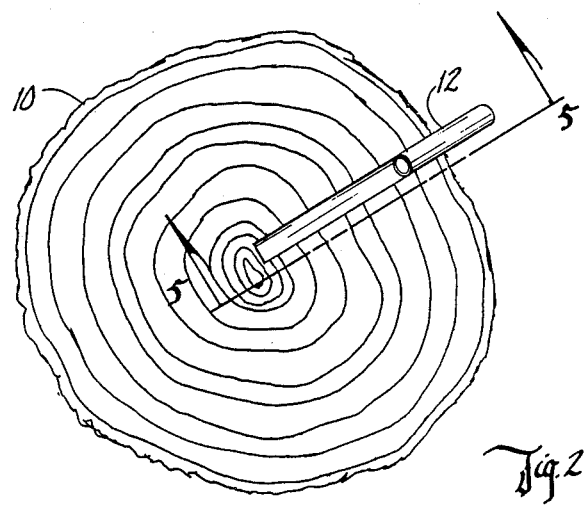
FIG. 2 shows a view along line 2—2 of FIG. 1 of the drain tubes.

Organo mercury compounds containing the methyl mercury complex are known to be highly lethal neurotoxins. In fact, the known highly effective neuro-toxin properties of methyl mercury resulted in a ban in use of methyl mercury in the 1950's. For this reason, any further investigations of its use as a fungicide for treatment of fungus diseases of deciduous trees was stopped.

The applicant has discovered that certain completely non-harmful, inorganic salts of mercury can be combined with methanol and injected into fungus infected deciduous trees; and, the naturally occurring microorganism population of the trees utilizes the injection as a nutrient, and, during the metabolic process, converts the non-harmful inorganic mercury salt, to the highly effective neuro-toxin organic mercury complex, methyl mercury. Importantly, this all occurs within the vascular system of the host tree. As a result, neither the tree-treating individuals nor the environment are subjected to highly lethal methyl mercury. In other words, a latentiated form of highly effective neuro-toxin methyl mercury has been developed. The latentiation process takes advantage of the metabolic processes of the microorganisms within the host tree, which convert the non-harmful inorganic mercury salt, in the presence of methanol which is a nutrient for the microorganisms, to the highly lethal organo-mercury complex, methyl mercury.

After injection into the vascular system of the tree with the treating composition of this invention, trees known to be infected with Dutch Elm disease, oak wilt, sycamore decline, and maple decline, have successfully survived for years with no evidence of reoccurring infection. In other words, the disease is either killed because the fungus is killed, or the treatment causes the disease to go into remission without any evidence of reoccurring flare-ups.

It is not precisely known why the treating composition of this invention works. However, without wishing to be bound by any theory, it is believed that the tree infecting fungus produces highly toxic wastes which cause a reaction by the cells within the tree vascular system. This reaction causes a cancerous type growth of cells within the vascular system to develop, which is referred to as "tylosis". This plugs the vascular veins and shuts off the effective transfer of food and water supply so that the food and water nutrients cannot effectively travel up or down the tree. The natural cell preservation system of the tree reacts too slow to the fungus produced toxin in order to be effective for treatment. However, if the treating composition of this invention is introduced into the xylem vessels, the normal transpiration stream within the tree distributes the treating composition in the crown of the tree, and from there it may be transferred throughout the vascular system to the trunk, limbs and twigs.

Analytical work performed on trees treated with the treating composition of this invention show less than one part per million of total mercury can be found in the twigs of the trees. It is believed that the amount should have been much higher, perhaps six to seven parts per mercury if the mercury was equally distributed through the vascular system. This indicates very strongly that the mercury is bound to the tissues close to the point of injection and that a less reactive metabolite from the mercury is released to act against the *Cerateocystis Ulmi*. This evidence strongly suggests that under the conditions inside the elm tree, some methyl mercury is synthesized by the metabolic process of the bacteria within the host tree. It is believed that the methanol which is a known nutrient for the normal occurring organisms within deciduous trees acts as a carrier for the mercury chloride. During the metabolic process by the bacteria, methyl mercury organo complex is formed in situ. The methyl mercury diffuses through the cell membranes and is quickly distributed throughout the tree at very low levels.

Bacterial species commonly occurring in these trees for which methanol is a known nutrient, are *pseudomonas syringae*. The methanol provides a nutrient for the growth of the *pseudomonas* species which then biometholate the inorganic non-harmful mercury compound.

In any event, test data on experimental trees for many years, including up to as many as 18, have demonstrated that the treating composition of this invention either places the disease in remission for very long periods of time, or simply arrests it by killing the fungus.

As heretofore mentioned, the essential treating compositions provide a combination of a non-lethal and non-harmful soluble inorganic mercury salt with methanol. The mercury salts which may be employed are mercuric chloride, other mercury halides, mercury nitrate, sulfate, acetate, phosphate, etc. Generally they can be thought of as inorganic, water and methanol soluble mercury salts. Not much of the inorganic mercury salt is needed, because as explained earlier, the mercury compounds essentially bind to the tissues at the point of injection in the tree, while the Pseudomonas bacteria slowly biometholate the mercury forming the lethal toxin methyl mercury, which is slowly released and moves gradually through the tree at very low levels of parts per million and/or parts per billion.

The preferred composition for the treatment of this invention comprises from about 0.1% by weight to about 0.15% by weight of a methanol soluble and water soluble inorganic mercuric salt, from about 95% to about 96% methanol, and from about 1% to about 5% of *Pseudomonas* bacterial mineral nutrients are a necessary ingredient. It is essential that the *Pseudomonas* bacterial mineral nutrients be added or the tree will burn out. The preferred mineral nutrients are a combination of ferrous sulfate and zinc sulfate, preferably from about 2.5% to about 3% ferrous sulfate, and from about 1% to about 2% by weight zinc oxide.

The best mode known at the time of the filing of this application for the treating composition of this invention comprises about 0.12% mercuric chloride, about 95.65% methanol, about 2.75% ferrous sulfate, and about 1.48% zinc oxide. The amount employed can be from one pint to about one gallon depending on tree size.

With continuing reference to the drawings, the method by which the treatment is applied to the tree, will now be described.

FIG. 1 shows a tree, after treatment by injection for Dutch Elm Disease. The tree 10 represents an Elm tree, infected with Dutch elm Disease. Of course prior to any treatment, the treating composition is mixed. The composition is simply mixed together, for purposes of this illustration we are assuming the best mode description of a treating composition, that is 0.12% mercuric chloride, 95.65% methanol, 2.75% ferrous sulfate, and 1.48% zinc oxide. The ingredients are stirred together until substantial solution and homogeneity is achieved. The tree shown in FIG. 1 is representative, and about 24 inches in diameter. For Dutch Elm Disease only, it is important that prior to any injection treatment, a drain tube is placed near the base of the tree and away from any flare roots, so that dripping from the drain tube will not be on the flare root. One drain tube 12 is placed at the base aimed towards the center of the tree, and for a 24 inch diameter tree, one is sufficient. Ideally, one additional drain tube 12 is added for each six inches of additional diameter. The drain tubes 12 are placed in the tree, and angled downwardly at approximately a 45° angle aimed towards the center of the tree. The size of the drain hole is typically a ⅜ths inch drain hole. The purpose of the drain hole or holes are to drain sap out of the tree vascular system to make room for the injected treating chemical. The relieved vascular pressure assures the injected treating chemicals will be easily accepted within the tree vascular system. The drain hole or holes should penetrate sufficiently far into the tree that they go well beyond the bark layer and into the heart of the tree.

Figure 3:
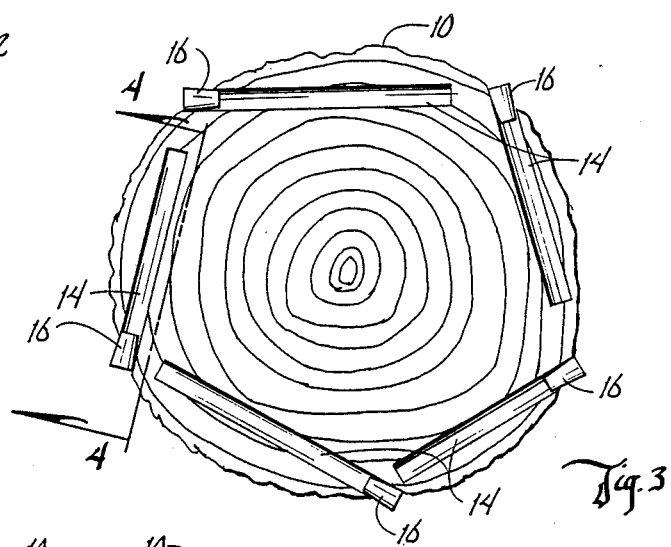
FIG. 3 shows a sectional view along line 3—3 of FIG. 1 of the injection holes.
Figure 4:
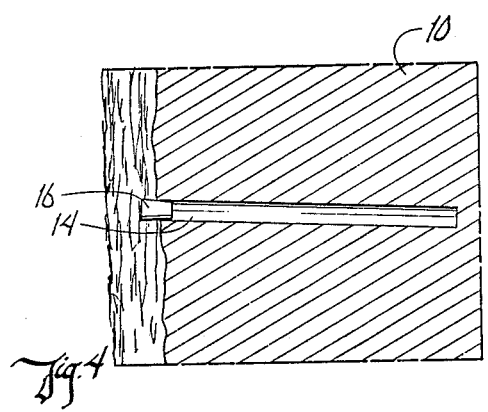
FIG. 4 is a view along line 4—4 of FIG. 3, showing the injection hole.
Figure 5:
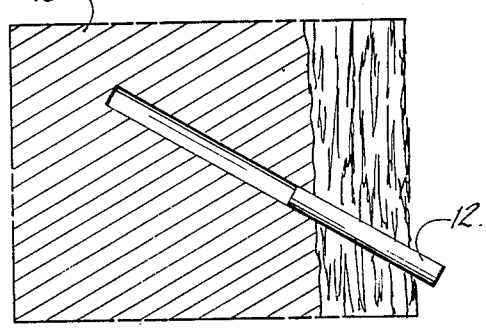
FIG. 5 is a view along line 5—5 of FIG. 2 showing the drain tube.

After the drain tube or tubes 12 have been inserted as previously described, the next step in the procedure is to move up the trunk of the tree (perhaps 12 to 16 inches) and place a series of injection bore holes 14. The injection bore holes are similar in all respects to the drain tube bore holes, except the drain holes are drilled upwardly to allow a downward drain of the sap, while injection holes are bored slightly downward, but at a sidewise 45° angle, and sidewise to contact as much xylem as possible (see FIG. 3). Again, a ⅜ths diameter bore hole has proven to be most satisfactory. The holes are bored, for a 24 inch diameter tree five are sufficient, with the important guideline being a sufficient number to get full coverage on each side of the tree. After the bore holes 14 are made at the slight downward angle and at a 45° angle sidewise from the center of the tree, they are filled with treating chemical composition as previously described, and plugs 16 inserted. Preferably, because the treating composition is easily absorbed, one should go around the tree and fill the injection bores 14 three separate times before plugs 16 are inserted. Plugs 16 are of two inch length, ⅜ths dowls, which are simply driven in with a hammer and countersunk below the bark. Thereafter, a tree wound dressing is placed over them to seal the tree. A suitable tree wound dressing is any of the available asphalt based dressings.

When this treatment is completed for Dutch Elm, the drain holes are simply left, causing no harm.

For treating trees other than Dutch Elm, no drain tubes are needed, but the procedure is otherwise exactly the same, except the drain hole is plugged and countersunk.

The following examples are offered to further illustrate but not limit the invention disclosed herein.

In each instance, the treating composition was the best mode embodiment of the invention and the treating method was as immediately above described. Any variations are specifically mentioned.

EXAMPLES ON TREATMENT OF DUTCH ELM

The examples reported in the following date are from Dutch Elm disease infected trees in Babler State Park, St. Louis County, Mo., which is 20 miles west of the City of St. Louis. In 1966, 100 elm trees in this area were selected as controls, and not treated. In addition, 100 other elm trees were selected as experimental treated trees and treated for Dutch Elm disease, in the manner heretofore mentioned. Thereafter, readings were taken in 1968, 1974 and 1980 on the trees. The treatment was done by the inventor, and others under his direction and control, supervised by the Missouri Department of Agriculture, and inspected by the United States Department of Agriculture under prescribed scientific method requirements of the United States Department of Agriculture. No one knew the composition except the inventor. After 14 years of study and evaluation, of the total number of treated trees, 70 remained alive, well and still growing. Of the selected 100 untreated control trees, in 1968 only 20 remained alive; in 1974, 17 of the original control remained alive, and in 1980, only 12 trees were found alive. Thus, only 12% of the untreated trees remained alive, with all the rest succumbing to Dutch Elm disease, whereas 70% of the treated trees remained alive, healthy and were growing.

This test, it should be noted, started with 200 trees located in a natural wood setting. No trimming was performed, nor other maintenance initiated.

Moreover, as to the 12 remaining untreated trees which are alive, it is believed that the majority of the untreated control trees are alive because of their proximity to the treated trees. In other words, substantial root grafting from the treated to the untreated trees transmitted the fungicide.

After this length of time, it is also apparent that no evidence of the injection holes were present and healing was complete. Moreover, when compared with the 1966 tree population, the entire area in 1980 was saturated with diseased, dead or dying elm trees. Yet, the treated trees survived and lived.

This St. Louis test is typical of tests which were run in Wisconsin from 1975 through 1980, in the City of Appleton, and in certain other midwestern cities.

EXAMPLES OF TREATMENT OF OTHER DEDICUOUS TREES

In 1975, a sample of 44 burr oak trees was selected on the Municipal Golf Course in Muscatine, Iowa. Ten of these were found to be diseased with oak wilt. An additional sample in the same area of eight controls was selected. The 44 trees were treated in the manner previously decribed, with the exception of the drain tubes which were omitted. Periodic examinations on a yearly basis have been made by the inventor. All 44 including the ten diseased trees, remain viable, healthy and have been growing. Injection wounds have totally healed. The eight controls which were not treated have succumbed to death from oak wilt. The controls have been removed.

In 1979, also in Muscatine, Iowa, a stand of red oak and white oak, totaling 16 trees, was treated. Of the 16, two were infected with oak wilt. Five additional trees were selected as controls and not treated. Of the controls, three have succumbed to oak wilt and been removed and two are in decline. The 16 treated trees, including the two infected ones, all are stable and show normal growth.

In 1981, 16 red oaks were selected at 1700 Cedar Street, Muscatine, Iowa, for treatment. Ten controls were selected in the same area. The treated trees are stable, and of the controls, all ten have succumbed to oak wilt.

In 1976, a stand of five sycamores showing evidence of sycamore decline were selected for treatment. Two controls were also selected. Test examinations have been run on an annual basis. The treated trees are stable, and show normal growth. Two untreated trees are in a state of severe decline. In 1980, 12 Norway maples were selected for treatment in an area known to have some evidence of maple decline, and three were selected as controls. All 12 are stable and showing normal growth, whereas the three controls succumbed to maple decline and had to be removed.

In all the tests described herein with respect to each of the cities mentioned herein, the testing was conducted on an experimental basis by the inventor, who periodically checked the trees, or had the trees checked by others who reported to him. The treatment of the trees was done by the inventor. No charges were made for the treatment and no one was told the formula or treating technique, except the United States Environmental Protection Agency under a secrecy agreement.

It therefore can be seen that the invention accomplishes each of its objectives.

What is claimed is:

1. A method of treating deciduous trees infected with fungi which produce toxins known to be harmful to trees, said method comprising:
   introducing into the vascular system of trees a small but effective amount of an active composition of methanol in combination with a soluble inorganic mercury salt and with a *Pseudomonas* bacterial nutrient.

2. The method of claim 1 wherein the mercury salt is a mercury halide salt.

3. The methoid of claim 2 wherein the mercury salt is mercuric chloride.

4. The method of claim 1 wherein the mercuric salt is selected from the group consisting of mercuric chloride, mercuric bromide, mercuric acetate, mercuric phosphate, mercuric sulfate, and mercuric nitrate.

5. The method of claim 1 wherein the active composition is introduced into the cambium layer of a tree.

6. The method of claim 5 wherein the active composition is introduced into the xylem.

7. A composition for treating fungus diseases of trees, comprising, in combination:
   a small but effective amount of a water and methanol soluble, inorganic mercuric salt, in association with methanol and a *Pseudomonas* bacterial nutrient.

8. The composition of claim 7, having the following formulation: from about 0.10% to about 0.15% by weight of mercuric chloride from about 95% to about 96% methanol; and from about 1% to about 5% of *Pseudomonas* bacterial mineral nutrients.

9. The composition of claim 8 wherein the mineral nutrients are a combination of ferrous sulfate, and zinc oxide.

10. The composition of claim 9 wherein the mineral nutrients are:
    from about 2.5% by weight to about 3.0% ferrous sulfate; and
    from about 1% by weight to about 2.0% by weight zinc oxide.

11. A method of preventing and/or treating Dutch Elm disease in elm trees, comprising:
   placing a drain outlet into the tree in its lower trunk extremities to allow some tree sap to drain and release pressure from the tree vascular system; and thereafter
   introducing into the vascular system of said tree, a small but effective amount of a treating composition which is from about 95% to about 96% of methanol, from about 0.10% to about 0.15% by weight of an inorganic mercuric salt, and from about 1% to 5% of a *Pseudomonas* bacterial mineral nutrient.

12. The method of claim 11 wherein the amount of treating composition used is from one pint to about one gallon per mature, adult tree.

13. A method of treating fungus infected deciduous trees, comprising:
   introducing into the vascular system of the tree a small but non-toxic and treatment effective amount of an inorganic water soluble mercuric salt in association with methanol, which is capable of being metabolized to a fungus-lethal methyl-mercury organic complex within the tree, by *Pseudomonas* bacterial species, living within the host tree.

* * * * *